United States Patent

Gutierrez et al.

[11] Patent Number: 5,391,823
[45] Date of Patent: Feb. 21, 1995

[54] PROCESS FOR THE PREPARATION OF 2,2'-OXYDISUCCINATE

[75] Inventors: Eddie N. Gutierrez, Ridgefield; Michael I. Hill, Ridgewood; Martina Santoso, North Brunswick; Donna Wu, North Plainfield; Shang-Ren Wu, Mahwah, all of N.J.

[73] Assignee: Lever Brothers Company, New York, N.Y.

[21] Appl. No.: 198,401

[22] Filed: Sep. 24, 1993

Related U.S. Application Data

[63] Continuation-in-part of Ser. No. 996,334, Dec. 23, 1992, abandoned, which is a continuation-in-part of Ser. No. 446,906, Dec. 6, 1989, abandoned.

[51] Int. Cl.$^6$ ............................................. C07C 59/125
[52] U.S. Cl. .................................................. 512/583
[58] Field of Search ......................................... 562/583

[56] References Cited

U.S. PATENT DOCUMENTS

5,001,245  3/1991  Nakairo et al. ................ 556/131
5,171,886  12/1992  Schultz ........................... 562/583

FOREIGN PATENT DOCUMENTS

486452  5/1992  European Pat. Off. .

Primary Examiner—Paul J. Killos
Attorney, Agent, or Firm—James J. Farrell

[57] ABSTRACT

A process for the preparation of 2,2'-oxydisuccinate from maleate, malate and alkaline earth metal hydroxide is disclosed which cooperatively control pH, temperature, time and ratio of reactants to effectively avoid substantial phase separation.

8 Claims, No Drawings

PROCESS FOR THE PREPARATION OF 2,2'-OXYDISUCCINATE

This is a continuation-in-part application of Gutierrez et al. Ser. No. 07/996,334, filed Dec. 23, 1992, now abandoned, which was a continuation-in-part application of Gutierrez et al. Ser. No. 07/446,906, filed Dec. 6, 1989, now abandoned.

BACKGROUND OF THE INVENTION

1. Field of the Invention

The invention relates to the preparation of the salt of 2,2'-oxydisuccinic acid by a process which produces the salt in reasonable times and temperatures while substantially avoiding phase separation or gelation of the reaction mixture. 2,2'-oxydisuccinic acid and salts thereof are effective sequestering agents and are useful as builders in detergent compositions for household, institutional and industrial use.

2. Related Art 2,2'-oxydisuccinic acid (ODS) and salts thereof are known and are known to have utility as sequestering agents and detergent builders. A disadvantage of ODS and salts thereof as detergent builders is that they may be relatively expensive to prepare.

U.S. Pat. No. 3,128,287 to Berg discloses a preparation of ODS salt by admixing maleic acid with an excess of hydroxide of calcium, barium, magnesium or strontium in the presence of water, then heating the reaction mixture from about one day to about one month at temperatures ranging from 50° C. to reflux temperatures. The process yields a mixture of malic acid and ODS. Berg's Example I teaches the preparation of ODS, wherein the aqueous mixture of maleic anhydride and calcium hydroxide is reacted at reflux (100° C. for 4 days. Subsequently, ODS salt is isolated from the product containing ODS and malic acid salts.

U.S. Pat. No. 3,635,830 to Lamberti et al., discloses the process for the preparation of ODS based on the process of Berg. The patent teaches separation/purification of two diastereoisomeric forms of ODS obtained by the Berg process. The patent also discloses detergent compositions comprising ODS or salts thereof as detergent builders.

U.S. Pat. No. 4,798,907 to MacBrair et al. discloses an improvement in the ODS-forming processes of Berg and Lamberti et al., wherein an alkali metal hydroxide, e.g. sodium hydroxide, is incorporated into a starting reaction mixture which also contains a divalent metal cation. To product yields of about 80% ODS, the process generally involves reacting the mixed starting materials in water for at least 12 hours at temperatures of about 20°–100° C. In McBrair the amount of the divalent metal cation used in less than stoichiometric.

European Patent 206,007 to Bush teaches a process for the preparation of ODS similar to the process of the MacBrair patent. Mixtures of inorganic base with water-soluble, inorganic salts of sodium, calcium or mixtures thereof may be used. a particularly preferred reactant combination constitutes maleic acid, malic acid, calcium hydroxide and sodium hydroxide. The ODS yield of about 60% is obtained in about 6 hours.

The MacBrair et al. and Bush patents rely on incorporation of alkali metal hydroxide into the reactant mixture to minimize gelation of the mixture and to increase yields of ODS. Alkali metal hydroxides indeed produce homogeneous solutions, but unlike the alkaline earth metal hydroxides, generate higher pHs and result in a gradual decomposition of ODS under the reaction conditions employed by the MacBrair et al. and Bush patents which is believed to produce fumarate. Thus, high temperatures for long periods of time must be avoided.

A workable and cost-efficient production of ODS salt must be directed towards optimizing the process conditions in such a manner that phase separation of the reaction mixture is substantially avoided while minimizing the reaction time. There have been different approaches to the problem of producing ODS at a lower cost. However, none of these approaches has been completely satisfactory.

Accordingly, it is an object of the present invention to provide a process which produces the salt of ODS.

This and other objects and advantages will appear as the description proceeds.

SUMMARY OF THE INVENTION

The attainment of the above objects is made possible by this invention which includes a preparation of the salt of ODS by a process comprising the steps of:

i dissolving
  a) Maleic anhydride, maleic acid or mixtures of these; and
  b) Malic acid including d, l and mixtures of d and l; in
  c) Water, in a ratio of 1.2 to 5.0 moles of maleic species to 1.0 moles of malic species to form an acid solution of mixture containing some undissolved solids;

ii mixing the acid solution or mixture with a slurry of alkaline earth metal hydroxide, to form a mixture, said slurry containing a stoichiometric amount of the alkaline earth metal hydroxide, preferably Ca(OH)$_2$, to neutralize said acid, plus about 10% in excess of this amount, but in any case sufficient to maintain the pH of the mixture at about 11.0 to 12.3 when measured at 25° C. and 20% solids. The slurry contains sufficient water so that the mixture of acid solution and slurry contains at least about 55% by weight water, preferably adding the acid solution or mixture to the hydroxide slurry; at solid loadings of about 36% or higher additional solid acid and hydroxide are preferably added to the mixture;

iii after forming said mixture, maintaining the temperature of said mixture at about 60° C. to 95° C. for about 2 to 8 hours, optionally employing an atmosphere inert to the reactants, such as nitrogen and the like.

In general, the process involves running the reaction at a sufficient temperature for a sufficient time to form the final product while maintaining the following parameters:

A. insuring solubility of the final ODS and other components in concentrations from about 5% up to about 45% to 50% by weight of solute by varying the temperature of reaction between about 60° C. where this higher amount of ODS and other components is substantially completely soluble up to about 95° C. where ODS and other components is only marginally soluble. Optionally, the reaction can be continued at temperatures lower than 60° C. to obtain higher yields, without encountering substantial phase separation.

B. Insuring that the solubility of the ODS and other components is never substantially exceeded at a particular temperature by varying the time at which the reaction is held to guarantee that the total concentration of ODS and other components do not substantially exceed their solubility limitations at the temperature in question. If phase separation occurs it is reversible but time consuming. The solubility of the calcium salt is important to avoid phase separation, keeping in mind the inverse nature of the calcium salt solubility, i.e., the salt is more soluble at cooler temperatures within the range. It should be noted that at low concentrations of solids, for example, concentrations of 20% then ratios of maleic to malic of less than 1.2 to 1 are sometimes employed to advantage.

Control of the molar ratio of the alkaline earth metal hydroxide to organic reactants, the ratio of maleate to malate, the amount of water in the reaction mixture and the reaction temperature of about 60° to 95° C. are critical to obtain the ODS salt product in about 5 hours and to avoid substantial phase separation of the reaction mixture.

In its broadest aspect, the invention provides a process for synthesizing the salt of ODS in about 5 hours at temperatures not greater than about 100° C. while substantially avoiding phase separation of the reaction mixture.

An alkaline earth metal salt of ODS may be isolated from other organic species contained in the reaction product obtained by the inventive process and converted to ODS (Formula I below)

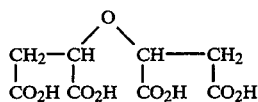

FORMULA I or ODS salts such as monovalent cation salts, ammonium salts, morpholinium salts, alkanol ammonium salts and mixtures thereof, by methods known in the art. Such methods are disclosed, for example, in U.S. Pat. No. 3,128,287 to Berg and U.S. Pat. No. 3,635,830 to Lamberti et al. discussed above and incorporated herein by reference. As noted, the 3,635,830 patent also discloses detergent compositions containing ODS or salts thereof.

In defining the ODS salt forming process of this invention it is intended to include both batch and continuous processes.

DETAILED DESCRIPTION OF THE INVENTION

The inventive process of this invention for obtaining the reaction product which contains the salt of ODS and in which gelation of the reaction mixture is substantially avoided is outlined as follows:

i dissolving
  a) Maleic anhydride, maleic acid or mixtures of these; and
  b) Malic acid including d, l, and mixtures of d and l, in
  c) Water in a ration of 1.2 to 5.0 moles of maleic species to 1.0 moles of malic species to form an acid solution or mixture;

ii mixing the acid solution or mixture with a slurry of alkaline earth metal hydroxide, to form a second mixture, said slurry containing a stoichiometric amount of the alkaline earth metal hydroxide, preferably Ca(OH)$_2$ to neutralize said acid plus about 10% in excess of this amount, but in any case sufficient to maintain the pH of the mixture at about 11.0 to 12.3 when measured at 25° C. and 20% solids, said slurry containing sufficient water so that said second mixture contains at least about 55% by weight water, preferably adding the acid solution or mixture to the hydroxide slurry;

iii after forming said second mixture, maintaining the temperature of said second mixture preferably at about 60° C. to 95° C. for about 2 to 8 hours, optionally employing an atmosphere inert to the reactants such as nitrogen and the like.

The process of this invention for the preparation of the salt of ODS includes forming an aqueous mixture of starting reactants containing a malate moiety, a maleate moiety and an alkaline earth metal hydroxide. The chemically suitable forms of malate and maleate reactants include acids and the anhydride of maleic acid. The molar ratio of maleate to malate is about 5.0:1 to about 1.2:1.

The alkaline earth metal hydroxide in the reaction mixtures of the inventive process is selected from the group consisting of barium hydroxide, strontium hydroxide or calcium hydroxide. The most preferred alkaline earth metal hydroxide for use in this invention is calcium hydroxide.

The ODS salt forming reaction of the present invention is conducted at high concentration in aqueous media to afford efficacy and high throughput. The amount of water present may vary and is preferably sufficient to permit the reaction to proceed with the amount of water being about 55% to 95%. The amount may, however, be more or less depending on design parameters.

Desirably, the reactants of the staring mixture for the process are combined in water using physical agitation. In the preferred embodiments of the invention, the alkaline earth metal hydroxide is mixed with an aqueous mixture of the malate and maleate moieties producing what is believed to be a soluble mixed calcium complex. The stability of this calcium salt mixture is dependent on the temperature and pH. It is believed that it is necessary to form this complex to achieve high yields of ODS. If the hydroxide is first mixed with maleate in the absence of malate, or malate in the absence of maleate, insoluble calcium maleate and calcium malate are produced which when mixed together produce an insoluble mixture and poor yields of ODS will usually be obtained. The reaction is carried out in an apparatus equipped with stirring means, e.g., on a laboratory scale, a mechanical stirring device is employed. The apparatus may also be equipped with a condenser for safety reasons and to provide some means of condensing water which evaporates, so that it returns to the reaction mixture. The reaction is conducted at atmospheric pressure.

The reaction temperature for the process ranges from about 60° C. to about 95° C., preferably from about 70° C. to about 90° C. To minimize phase separation the reaction temperature is maintained for at least about 2 hours and preferably no longer than about 8 hours at temperatures ranging from 60° C. to 95° C. The aqueous reaction product typically contains a mixture of 2,2'-oxydisuccinate, malate, maleate and fumarate. Optionally the reaction can be continued at temperature lower than about 60° C. to obtain higher yields, without encountering substantial phase separation.

The reaction products obtained by the processes of this invention contain the alkaline earth metal salt of ODS and may be worked up by methods known in the art. Generally, the work up comprises the steps of reduction of calcium content in the product mixture and acidification or conversion into monovalent cation salts, ammonium salts, morpholinium salts, alkanol ammonium salts and mixtures thereof.

The calcium content of the reaction products may be reduced by conventional means. Removal of calcium can be carried out in a number of ways known in the art. In general, simply adding a calcium precipitating material will suffice. Such calcium precipitating materials include alkali metal carbonate, pyrophosphate, sulfates, bicarbonate and/or alkali metal silicate and mixtures thereof, for example, the addition of sodium carbonate will convert the alkaline earth metal salt obtained to the sodium salt. The resulting calcium precipitate can thereafter be removed from the aqueous reaction product mixture by filtration. In an alternative mode, removing calcium from the aqueous reaction product mixtures involves treatment of said mixtures with an appropriate insoluble ion exchange resin or zeolite. No matter what technique is employed, the calcium content of the ODS salt prepared by methods herein should desirably be reduced to the extent that calcium is present in an amount of no more than about 1.0% of the ODS salt and preferably less than 0.2%, in order to form compositions particularly suitable as detergent builders. This can be accomplished by the method of defensive publication T 101,805.

ODS salts formed herein can also be treated, after calcium removal, in a further step, using organic or aqueous solvent extraction to remove excess reactants, such as maleates, or organic reaction by-products, such as fumarates. This can, for example, be accomplished by conventional salt separation procedures using a solvent such as a mixture of methanol and water (4:1 v/v) in which these excess reactants and reaction by-products are relatively soluble and in which the desired ODS salt is relatively insoluble as disclosed in U.S. Pat. No. 5,068,420.

At any stage after the ODS salt formation, and after reducing the calcium salt content the reaction product can be concentrated by removal of water to the desired extent. Water removal can, for example, after calcium removal, involve substantially complete drying of the reaction product mixture, e.g., by spray drying, so that the ODS salt is recovered in solid, e.g., granular, form. The sodium salt of ODS in the form of aqueous liquid may be utilized directly in the preparation of detergent compositions or laundry additive products of the types more fully described hereinafter.

It is possible, if desired, to acidify the product mixtures using conventional acidification or ion exchange techniques to convert the ODS salts therein to their free acid form. Normally, however, the ODS materials of this invention can, after calcium depletion or complete replacement by sodium, be used as builders in their water-soluble salt form, and such acidification is therefore not usually necessary or desirable.

When converted into suitable form, the ODS salts can be used as sequestering builders in a wise variety of detergent or laundry additive compositions.

Detergent compositions incorporating the ODS salt prepared using the processes of this invention contain as essential components from about 0.5% to about 98% of a surfactant and from about 2% to about 99.5% of the ODS compounds as a detergency builder, generally in sodium-salt form. Surfactants that are useful in the present invention are the anionic (soap and nonsoap), nonionic zwitterionic and ampholytic compounds. The chemical nature of these detergent compounds is not an essential feature of the present invention. Moreover, such detergent compounds are well known to those skilled in the detergent art and the patent and printed literature are replete with disclosures of such compounds. Typical of such literature are "Surface Active Agents" by Schwartz and Perry and Berch, the disclosures of which are incorporated by reference herein. The ODS builder can be used either as the sole builder or where desired can be used in conjunction with other well-known builders, examples of which include water-soluble salts of phosphates, pyrophosphates, orthophosphates, polyphosphates, phosphonates, carbonates, polyhydroxysulfonates, polyacetates, carboxylates, polycarboxylates, succinates and the like.

In addition to the surfactant and builder there may be optionally present additional ingredients which enhance the performance of the detergent composition. Typical examples thereof include the well known soil suspending agents, hydrotropes, corrosion inhibitors, dyes, perfumes fillers, optical brighteners, enzymes, suds boosters, suds depressants, germicides, anti-tarnishing agents, cationic detergents, softeners, bleaches, buffers and the like.

The detergent compositions of the present invention may be in any of the usual physical forms for such compositions, such as powders, beads, flakes, bars, tablets, noodles, liquids, pastes and the like. The detergent compositions are prepared and utilized in the conventional manner. The wash solutions thereof desirably have a pH from about 7 to about 12, preferably from bout 9 to about 11.

In addition to their utility as builders in detergent and laundry additive compositions, the ODS salts of the invention can, after reducing their calcium content, also be utilized in other contexts wherein water hardness sequestration is required. Other uses are provided in water softening compositions, devices and methods and boiler descaling compositions and methods. It is also theorized that ODS can complex heavy metals which react with bleach and thus can stabilize bleach.

It should also be noted that when ODS is employed as the free acid or as partly neutralized salt it has utility in metal cleaning composition under pH conditions of about 2 to about 5. The following examples are designed to illustrate, but not to limit, the practice of the instant invention. All percentages and parts herein are by weight unless indicated otherwise. All ratios herein are mole ratios unless indicated otherwise. D L-malic acid is used in the Examples unless indicated otherwise.

Reaction mixture samples and reaction products were analyzed by HPLC and/or NMR. The HPLC analysis is carried out using a Hitachi instrument. The mobile phase is a 30/70 acetonitrile/water mixture with 0.75 g/l of 85% phosphoric acid at a pH of about 3 to 4. The column is an RP/SAX Regis 25 cm×4.6 mm in dimension. The flow rate is 1.5 ml/minute. The wavelength at which the detector is set is 210 nm. Samples are diluted with the mobile phase. Quantification is done using an external standard. The volume of the injections used are 50 $\mu$l.

The NMR is a 200 MHz Bruker model. Samples are prepared by ion exchanging the calcium salts, followed by neutralization of the acids with sodium carbonate and dissolution in $D_2O$. Peak assignments are as follows:

Fumaric 6.28 δ
Maleic 5.78 δ
Malic CH 4.1 to 4.3 δ
 CH$_2$ 2.0 to 2.5 δ (overlap with ODS)
ODS CH 3.83 to 3.59 δ
 CH$_2$ 2.0 to 2.5 δ (overlap with malic)

EXAMPLES

Examples 1–8

Maleic anhydride, 15.16 g (0.155 mole), is dissolved in 50 ml water, followed by 15.94 (0.119 mole) malic acid. This solution is gradually added to a slurry of calcium hydroxide 22.3 g (0.3 mole) maintained at a temperature of about 20° C. and containing sufficient water so that the final solution contains a known % solids. The temperature is then raised to 65°–70° C. for 4 hours and then 13–17 hours at 60° C. Weight % calculated by NMR.

Maleic anhydride, 27.5 g (028 mole), is dissolved in 50–55 ml water, followed by 29 g (0.22 mole) malic acid. Some undissolved solids will be present at this stage. This is necessary in order to have sufficient water to slurry the Ca(OH)$_2$. This mixture is gradually added to a slurry of calcium hydroxide 40.5 g (0.55 mole) maintained at a temperature of about 40° C. containing sufficient water so that the final solution contains a known % solids. The temperature is then raised to 65°–70° C. for 4 hours and then 116 hours at varying temperatures. The temperature and times for Example 5 are 4 hours at 70°; 72 hours at 50°; 88 hours (weekend) at 45° C. and 6 hours at 70°. Weight % calculated by NMR.

To a mixture of maleic acid and malic acid, according to the molar ratios listed in the table below, is added enough water so that the final concentration of solids is in the range of 20–30%. Solid calcium hydroxide, according to the amounts also listed, is added while the temperature is maintained at 10° C. during the addition. The temperature of reaction is then held at 75° C. for 11–26 hours.

| | REACTANTS (MOLAR RATIO) | | | | TOTAL REACTION TIME | PRODUCTS (WT %) | | | |
|---|---|---|---|---|---|---|---|---|---|
| | MALEIC | MALIC | Ca(OH)$_2$ | SOLID (%) | (Hours) | ODS | MALIC | MALEIC | FUMARIC |
| 6 | 1 | 1 | 2.2 | 20 | 11 | 78 | 12 | 9 | 1 |
| 7 | 1.2 | 1 | 2.4 | 25 | 20 | 76 | 13 | 9 | 2 |
| 8 | 1.2 | 2 | 2.4 | 30 | 26 | 76 | 12 | 11 | 1 |

In Example 6 a 1:1 ratio is operative because of the total solids loading of 20%.

Example 9

Maleic acid, 92.34 g (0.8 mole), and malic acid, 89.78 g (0.67 mole), are dissolved in 174 ml water. This solution is added to a slurry of 119.66 g (1.62 mole) of calcium hydroxide in 235.25 ml water while the temperature of addition is maintained at 50°–60° C. The temperature is then held at 60° C. for 5 hours then lowered to 40° C. Weight % determined by HPLC and in one case NMR.

| TIME AND TEMPERATURE | ODS | MALIC | MALEIC | FUMARIC | ANALYSIS |
|---|---|---|---|---|---|
| 5 hrs. @ 60° C. | 80 | 9 | 11 | — | HPLC |
| 5 hrs. @ 60° C. & 16 hrs. @ 40° C. | 87 | 6 | 7 | — | HPLC |
| 5 hrs. @ 60° C. & 40 hrs. @ 40° C. | 93 | 3 | 3 | 1 | NMR |
| | 88.1 | 2.5 | 6.8 | 2.5 | HPLC |

Example 10

| | REACTANTS (MOLAR RATIO) | | | | TOTAL REACTION TIME | PRODUCTS (WT %) | | | |
|---|---|---|---|---|---|---|---|---|---|
| | MALEIC | MALIC | Ca(OH)$_2$ | SOLID (%) | (Hours) | ODS | MALIC | MALEIC | FUMARIC |
| 1 | 1.3 | 1 | 2.5 | 25 | 20 | 79 | 13 | 7 | 1 |
| 2 | 1.3 | 1 | 2.5 | 30 | 17 | 87 | 9 | 4 | 0 |
| 3 | 1.3 | 1 | 2.5 | 36 | 21 | 84 | 10 | 3 | 2 |

Maleic acid, 51.04 g (0.44 mole), and malic acid, 50 g (0.37 mole), are dissolved in 80 ml water. This solution is added to a slurry of 65.86 g (0.89 mole) of calcium hydroxide in 235.25 ml water while the temperature of addition is maintained at 50°–55° C. The temperature is then held at 60° C. for 5.5 hrs. then at 45° C. for 16 hrs. Weight % calculated by NMR and HPLC.

| ODS | MALIC | MALEIC | FUMARIC | ANALYSIS |
|---|---|---|---|---|
| 90 | 5.0 | 5 | — | NMR |
| 86 | 0.6 | 11.4 | 1.2 | HPLC |

| | REACTANTS (MOLAR RATIO) | | | | TOTAL REACTION TIME | PRODUCTS (WT %) | | | |
|---|---|---|---|---|---|---|---|---|---|
| | MALEIC | MALIC | Ca(OH)$_2$ | SOLID (%) | (Hours) | ODS | MALIC | MALEIC | FUMARIC |
| 4 | 1.3 | 1 | 2.5 | 40 | 17 | 81 | 9 | 8 | 1 |
| 5 | 1.3 | 1 | 2.5 | 45 | 120 | 80 | 10 | 8 | 2 |

Example 11

Maleic acid, 51.04 g (0.44 mole), and l-malic acid, 49.6 g (0.37 mole), are dissolved in 100 ml water. This solution is gradually added to a slurry of 65.9 g (0.89 mole) of calcium hydroxide. The solution is heated to 68° C. for four hours and then lowered and maintained at 45° C. for 42 hours.

| ODS  | MALIC | MALEIC | FUMARIC | ANALYSIS |
|------|-------|--------|---------|----------|
| 90   | 5     | 4      | 1       | NMR      |
| 80.6 | 8.6   | 7.3    | 3.2     | HPLC     |

Example 12–16

168.8 g (1.20 Mole) of malic acid and 181.0 g (1.56 Mole) of maleic acid were dissolved in 396.5 g of water. This acid solution was added to a slurry of calcium hydroxide and water in a stirred, 2 liter jacketed reaction vessel at 25° C. This slurry consisted of 594.7 g of water, 202.4 g (2.76 moles) of calcium hydroxide, plus enough additional calcium hydroxide to bring the pH of the mixture of the specified value (approximately 20 g). After this addition, the mixture was heated to the specified temperature, and held at this temperature for 24 hours. A sample was then taken for HPLC analysis. The yield of ODS is shown below.

| Experiment | pH @ 25° C. | Temperature | Yield |
|------------|-------------|-------------|-------|
| 12         | 11.8        | 65° C.      | 74%   |
| 13         | 11.4        | 60° C.      | 76%   |
| 14         | 11.2        | 65° C.      | 75%   |
| 15         | 10.9        | 65° C.      | 56%   |
| 16         | 10.8        | 60° C.      | 31%   |

Examples 17–21

107.2 g (0.80 mole) of malic acid and 120.6 g (1.04 mole) of maleic acid were dissolved in 553.8 g of water. This acid solution was added to a slurry of 149.5 g (2.02 moles) of calcium hydroxide and 624.4 g of water in a stirred, 2 liter jacketed reaction vessel at the specified temperature, and held at this temperature for the total specified reaction time. If gelation occurred, the experiment needed to be aborted. If gelation did not occur, a sample was taken for HPLC analysis. The results are shown below.

| Experiment | Temperature | Reaction Time | Result                   |
|------------|-------------|---------------|--------------------------|
| 17         | 60° C.      | 24 hours      | 81% yield                |
| 18         | 70° C.      | 9 hours       | gelation-phase separation|
| 19         | 80° C.      | 4 hours       | 61% yield                |
| 20         | 90° C.      | 6 hours       | 61% yield                |
| 21         | 100° C.     | 4 hours       | gelation-phase separation|

Example 22

A) 5:1 Maleic to Malic

Maleic anhydride 14.7 g (0.15 mole), is dissolved in 25 ml water, followed by 4.0 (0.03 mole) malic acid. This solution is gradually added to a slurry of calcium hydroxide 19 g (0.25 mole) maintained at a temperature of about 50°–55° C. containing sufficient water so that the final solution contains a known % solids. The temperature is then raised to 65°–70° C. for 6 hours and then 13–17 hours at 40° C. Weight % calculated by NMR.

| ODS   | MALIC | MALEIC | FUMARIC |
|-------|-------|--------|---------|
| 64.5% | 5.2%  | 16.5%  | 3.3%    |

This shows a ratio of 5:1 maleate to malate.

B) 6:1 Maleic to Malic

Maleic anhydride 17.6 g (0.18 mole), is dissolved in 31 ml water, followed by 4.0 g (0.03 mole) malic acid. This solution is gradually added to 20.5 g (0.26 moles) of Ca(OH)$_2$ slurried in 35 ml of water. After mixing for a few minutes, the mixture became unstirrable and generally solid. After heating for 3 hours at 65° C. the solid dispersed and the heterogeneous mixture became stirrable. After stirring for an additional 6 hours at 65° C. and 13–17 hours at ambient and again 3 hours at 65° C. The mixture was analyzed. Weight % calculated by NMR:

| ODS   | MALIC | MALEIC | FUMARIC |
|-------|-------|--------|---------|
| 32.9% | 6.5%  | 59.1%  | 1.4%    |

Thus a 6:1 ratio gives yields which are too low to be practicable.

Example 23

Maleic anhydride, 6.8 g (0.07 mole), is dissolved in 10 ml water, followed by 7.5 g (0.056 mole) malic acid. This solution is gradually added to a slurry of calcium hydroxide 10.2 g (0.134 mole) in 26 ml of water and maintained at a temperature of about 40° C. The temperature is then raised to 65°–70° C. for 6–7 hours and then stirred 13–17 hours at room temperature. Weight % calculated by NMR.

| ODS   | MALIC | MALEIC | FUMARIC |
|-------|-------|--------|---------|
| 69.4% | 13.3  | 16.0   | 1.2     |

This product is recovered as the calcium salt and analyzed for sodium. The sodium content is 180 parts per million; 0.018% of the salt and is present as a contaminant.

This sodium content is a typical contaminant for the reactions described herein as well as for most chemical reactions.

Example 24

A) 7.5 g (0.056 moles) of malic acid are dissolved in 8 ml of water and added to a slurry of 10.2 (0.134 moles) of Ca(OH)$_2$ in 20 ml of water and mixed. After 5 minutes, 8.0 g (0.069 moles) of maleic acid dissolved in 8 ml of water are added to the above mixture and heated at 70° C. for 5–6 hours, then stirred 15–16 hours at room temperature and the product is collected. The weight % calculated by NMR is as follows:

| ODS  | MALIC | MALEIC | FUMARIC |
|------|-------|--------|---------|
| 2.9% | 56.8% | 44.7%  | 1.4%    |

Example 24 (Continued)

B. 8.0 g (0.069 moles) of maleic acid is dissolved in 8 ml of water and added to a slurry of 10.2 g (0.134 moles)

of Ca(OH)$_2$ in 20 ml of water and mixed. After 5 minutes 7.5 g (0.056 moles) of malic acid dissolved in 8 ml of water are added to the above mixture and heated at 70°–75° C. for 6–7 hours and the product is collected. The weight % calculated by NMR is as follows:

| ODS | MALIC | MALEIC | FUMARIC |
|---|---|---|---|
| 3.7% | 48.5% | 47.5% | 0.3% |

This example shows the criticality of mixing both maleic and maleic species prior to addition of the Ca(OH)$_2$.

Example 25

Maleic anhydride, 12.3 g (0.126 mole), is dissolved in 34.5 ml water, followed by 14 g (0.104 mole) of malic acid. This solution is gradually added to a slurry of calcium hydroxide 17.5 g (0.23 mole) in 34 ml of water. This is stirred and maintained at a temperature of about 40° C. or less. The pH is 7.5 and is raised to pH 10.5 with 0.1 g Ca(OH)$_2$. This forms a hazy initial mixture. The temperature of the mixture is then raised to 50° C. for 2 hours and then for 2 hours at 65°–70° C. At this point, a thick insoluble solid mixture results. Weight % calculated by NMR is as follows:

| ODS | MALIC | MALEIC |
|---|---|---|
| 0% | BALANCE TO 100% | |

This Example shows that a pH of 10.5 is inoperable.

Example 26

(Comparative)

Into one flask 9.8 g (0.1 mole) maleic anhydride is dissolved in 55.3 g water. Into a second flask 13.4 g (0.1 mole) of calcium hydroxide is dissolved in 55.3 ml of water. 8.2 g (0.107) of malic acid is added to each of the flasks, the mixtures stirred and then mixed together in a 250 ml, 3 neck round bottom flask. The mixture is stirred for 30 min. at room temperature and then heated to 70° C. Samples are periodically removed for NMR analysis, by acidifying with ion exchange resin and treating with Na$_2$CO$_3$ to a pH of about 9.

| No. of Hours | ODS | MALIC | MALEIC | FUMARIC |
|---|---|---|---|---|
| 4.0 | 11.1 | 39.8 | 49.1 | — |
| 20.5 | 39.0 | 39.0 | 23.6 | 1.2 |
| 28 | 37.1 | 38.8 | 22.0 | 2.1 |
| 44.5 | 35.7 | 38.4 | 17.1 | 8.7 |

This shows that separate preparation of calcium malate and calcium maleate with subsequent mixing does not produce high yields of ODS.

Example 27

(Comparative)

1.05:1 maleic: malic (35% solids)

A solution containing 45.24 g (0.39 mole) maleic acid, 50 g (0.37 mole) malic acid and 85 ml water is prepared. The acid solution is added to the slurry of calcium hydroxide at 45°–50° C. but tacky gels are formed immediately following the addition of acids. The reaction was aborted because of serious phase separation.

It is understood that the examples and embodiments described herein are for illustrative purposes only and that various modification or changes in the light thereof will be suggested to persons skilled in the art and are to be included within the spirit and purview of this application and the scope of the appended claims.

What is claimed is:

1. A process for preparing 2,2'-oxydisuccinic acid comprising:
   i dissolving
      a) maleic anhydride, maleic acid or mixtures of these; and
      b) malic acid selected from the group including d-malic acid, l-malic acid and mixtures of these, in
      c) water, in a ratio of 1.2 to 5.0 moles of maleic species to 1.0 moles of malic species to form an acid solution or mixture;
   ii mixing the acid solution or mixture with a slurry of alkaline earth metal hydroxide, to form a second mixture, said slurry containing a stoichiometric amount of alkaline earth metal hydroxide to neutralize said acid plus about 10% in excess of said amount but in any case sufficient to maintain the pH of said mixture at about 11.0 to 12.3 when measured at 25° C. and 20% solids, said slurry containing sufficient water so that said second mixture contains at least about 55% by weight water;
   iii after forming said second mixture, maintaining the temperature of said second mixture at about 60° C. to 95° C. for about 2 to 8 hours, optionally employing an inert atmosphere.

2. A process as defined in claim 1 wherein the reaction is extended for a period of about 24 hours at a temperature of less than 60° C.

3. A process as defined in claim 1 wherein the alkaline earth metal hydroxide is calcium hydroxide.

4. A process as defined in claim 1 wherein the mole ratio of said a) to said b) is 1.2 to 1.

5. A process as defined in claim 1 wherein the 2,2'-oxydisuccinic acid is recovered from the reaction mixture.

6. A method for purifying the product obtained from claim 1 by contacting the reaction mixture from step ii with a mixed methanol/water solvent after reducing the calcium content of the product.

7. A process as defined in claim 1 wherein the concentration of maleic and malic species at the beginning of the reaction as the calcium salt is about 5% to 45%.

8. A process as defined in claim 1 wherein the concentration of maleic and malic species at the beginning of the reaction as the calcium salt is about 30% to 40%.

* * * * *